(12) United States Patent
Rutledge et al.

(10) Patent No.: US 12,150,493 B2
(45) Date of Patent: Nov. 26, 2024

(54) CHILD SOOTHING DEVICES COMPRISING ARTIFICIAL MUSCLES

(71) Applicant: Toyota Motor Engineering & Manufacturing North America, Inc., Plano, TX (US)

(72) Inventors: Erin J. Rutledge, Tipton, MI (US); Michael P. Rowe, Pinckney, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 975 days.

(21) Appl. No.: 17/160,548

(22) Filed: Jan. 28, 2021

(65) Prior Publication Data
US 2022/0232903 A1 Jul. 28, 2022

(51) Int. Cl.
*A41B 13/06* (2006.01)
*A61M 21/00* (2006.01)
*A61M 21/02* (2006.01)

(52) U.S. Cl.
CPC ............ *A41B 13/06* (2013.01); *A61M 21/02* (2013.01); *A41B 2400/32* (2013.01);
(Continued)

(58) Field of Classification Search
CPC . A41B 13/06; A41B 2400/32; A41B 2500/00; A61M 21/02; A61M 2021/0022;
(Continued)

(56) References Cited

U.S. PATENT DOCUMENTS

| 6,142,963 A | 11/2000 | Black et al. |
| 8,863,329 B2 | 10/2014 | Gangan et al. |

(Continued)

FOREIGN PATENT DOCUMENTS

| CN | 206006719 U | 3/2017 |
| CN | 107596519 A | 1/2018 |

(Continued)

OTHER PUBLICATIONS

"Zen sleepwear™" (https://www.nestedbean.com/pages/zen-sleepwear), accessed Aug. 10, 2020.
(Continued)

*Primary Examiner* — Thaddeus B Cox
*Assistant Examiner* — Joshua Daryl D Lannu
(74) *Attorney, Agent, or Firm* — Dinsmore & Shohl LLP

(57) ABSTRACT

A child soothing device includes a soothing structure includes an outer layer and an inner layer, and one or more artificial muscles disposed between the inner layer and the outer layer of the soothing structure and communicatively coupled to a controller. Each of the one or more artificial muscles includes a housing comprising an electrode region and an expandable fluid region and a dielectric fluid housed within the housing. Each of the one or more artificial muscles also includes an electrode pair positioned in the electrode region of the housing, the electrode pair including a first electrode and a second electrode. The electrode pair is actuatable between a non-actuated state and an actuated state such that actuation from the non-actuated state to the actuated state directs the dielectric fluid into the expandable fluid region, expanding the expandable fluid region, thereby applying pressure to the inner layer of the soothing structure.

17 Claims, 16 Drawing Sheets

(52) U.S. Cl.
CPC .. *A41B 2500/00* (2013.01); *A61M 2021/0022* (2013.01); *A61M 2021/0066* (2013.01); *A61M 2205/3331* (2013.01); *A61M 2230/06* (2013.01); *A61M 2240/00* (2013.01)

(58) Field of Classification Search
CPC .. A61M 2021/0066; A61M 2205/3331; A61M 2230/06; A61M 2240/00; A61M 2205/3553; A61M 2205/8206; A61M 2021/0061; A61M 2205/10; A61M 2205/3344; A61M 2205/505; A61M 2230/50
See application file for complete search history.

(56) References Cited

U.S. PATENT DOCUMENTS

| | | | |
|---|---|---|---|
| 10,441,743 | B1 | 10/2019 | Mckamy |
| 2014/0101862 | A1* | 4/2014 | Misaki ............... A61G 7/05769 5/710 |
| 2014/0275742 | A1 | 9/2014 | Andrew |
| 2017/0348187 | A1 | 12/2017 | Piccirillo |
| 2018/0027988 | A1* | 2/2018 | Poodeh ............... A47G 9/1027 |
| 2018/0228222 | A1 | 8/2018 | Barski et al. |
| 2019/0208832 | A1 | 7/2019 | Geraghty |
| 2019/0313702 | A1 | 10/2019 | Karp et al. |
| 2020/0196685 | A1 | 6/2020 | Williams |
| 2021/0003149 | A1* | 1/2021 | Keplinger ............... F15B 15/10 |

FOREIGN PATENT DOCUMENTS

| | | |
|---|---|---|
| CN | 208192169 U | 12/2018 |
| CN | 209750610 U | 12/2019 |
| DE | 202014011042 U1 | 7/2017 |
| WO | 2018075566 A1 | 4/2018 |

OTHER PUBLICATIONS

"Improved relaxation & sleep" (https://dreamlandbabyco.com/), accessed Aug. 10, 2020.

E. Acome, et al., "Hydraulically Amplified Self-Healing Electrostatic Actuators With Muscle-Like Performance," Science Journal, Jan. 5, 2018: vol. 359, Issue 6371, pp. 61-651, Department of Mechanical Engineering & Materials Science and Engineering Program, University of Colorado, Boulder, CO 80309, USA.

* cited by examiner

CHILD SOOTHING DEVICES COMPRISING ARTIFICIAL MUSCLES

TECHNICAL FIELD

The present specification generally relates to child soothing devices and, in particular, to child soothing devices that include artificial muscles for providing gentle pressure to simulate a caregiver.

BACKGROUND

When a baby is born, the need for touch, warmth, and to be held can be important for health and development purposes. Current options do not harness the stimulation of touch or provide the feeling as though the baby is being held while regulating body temperature. While swaddling blankets and baby sleep sacks embody the main goal of comforting a baby, these are merely articles of clothing that do not contain technology that would allow for the newborn to feel the sensation of touch or as though it is being held.

Accordingly, there exists a need for improved simulation caregiver simulation for babies.

SUMMARY

In one embodiment, a child soothing device includes a soothing structure having an outer layer and an inner layer, and one or more artificial muscles disposed between the inner layer and the outer layer of the soothing structure and communicatively coupled to a controller. Each of the one or more artificial muscles includes a housing comprising an electrode region and an expandable fluid region and a dielectric fluid housed within the housing. Each of the one or more artificial muscles also includes an electrode pair positioned in the electrode region of the housing, the electrode pair including a first electrode and a second electrode. The electrode pair is actuatable between a non-actuated state and an actuated state such that actuation from the non-actuated state to the actuated state directs the dielectric fluid into the expandable fluid region, expanding the expandable fluid region, thereby applying pressure to the inner layer of the soothing structure.

In another embodiment, a method for actuating a child soothing device includes providing a voltage using a power supply electrically coupled to an electrode pair of an artificial muscle, the artificial muscle disposed between an inner layer and an outer layer of a soothing structure of the child soothing device. The artificial muscle includes a housing having an electrode region and an expandable fluid region. The electrode pair is positioned in the electrode region of the housing. The electrode pair includes a first electrode and a second electrode. A dielectric fluid is housed within the housing. A pressure sensor is affixed to the housing and communicatively coupled to a controller. The method also includes applying the voltage to the electrode pair of the artificial muscle, thereby actuating the electrode pair such that the dielectric fluid is directed into the expandable fluid region of the housing and expands the expandable fluid region, thereby applying pressure to the inner layer of the soothing structure.

In yet another embodiment, a child soothing system includes a child soothing device having a soothing structure which includes an outer layer and an inner layer along with network interface hardware communicatively that is coupled to a sensor device and configured to receive heartbeat data from the sensor device pertaining to a user wearing the sensor device. The child soothing device further includes one or more artificial muscles disposed between the inner layer and the outer layer of the soothing structure and communicatively coupled to a controller. Each of the one or more artificial muscles includes a housing comprising an electrode region and an expandable fluid region and a dielectric fluid housed within the housing. Each of the one or more artificial muscles also includes an electrode pair positioned in the electrode region of the housing, the electrode pair including a first electrode and a second electrode. The electrode pair is actuatable between a non-actuated state and an actuated state such that actuation from the non-actuated state to the actuated state directs the dielectric fluid into the expandable fluid region, expanding the expandable fluid region, thereby applying pressure to the inner layer of the soothing structure. The child soothing system also includes the sensor device that is communicatively coupled to the child soothing device and is configured to detect the heartbeat of the user and provide heartbeat data corresponding to the user to the child soothing device.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
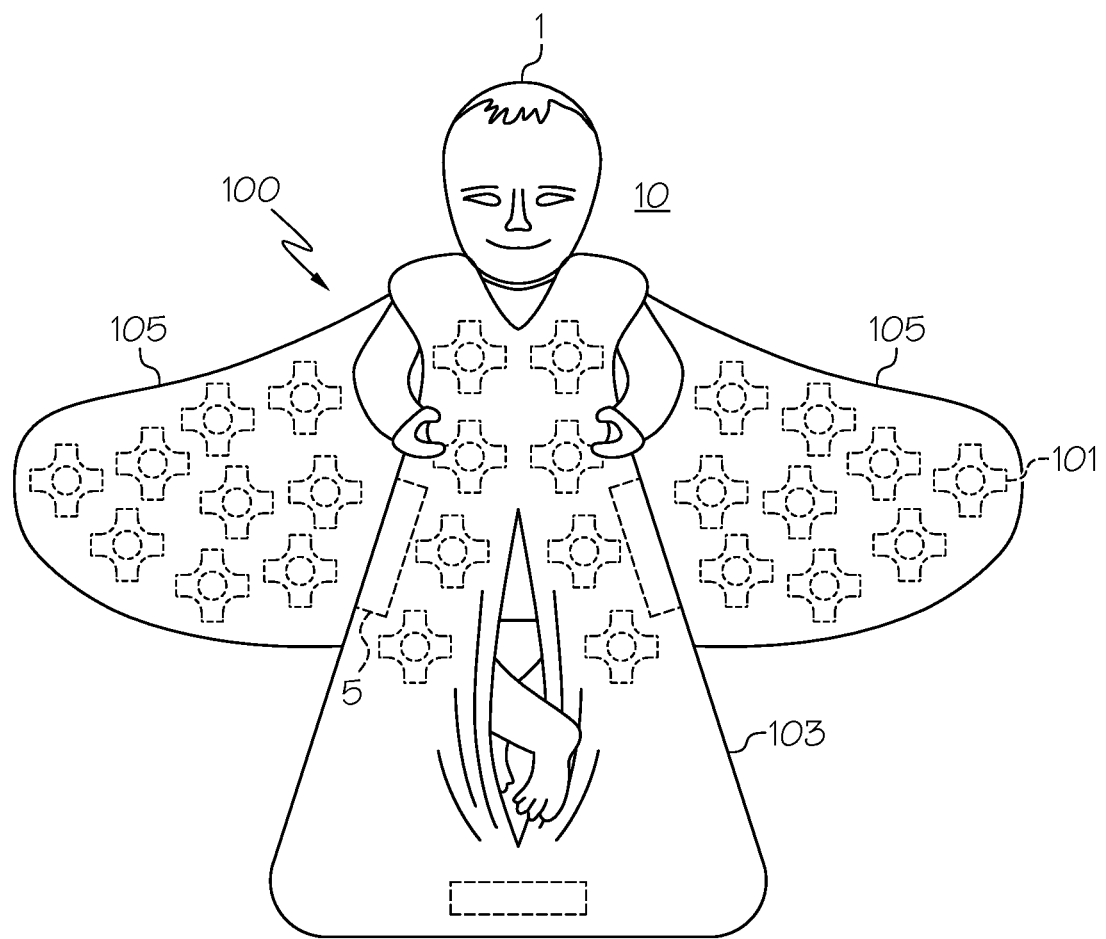
FIG. 1A schematically depicts a swaddle child soothing device with open flaps, according to one or more embodiments shown and described herein.
Figure 1B:
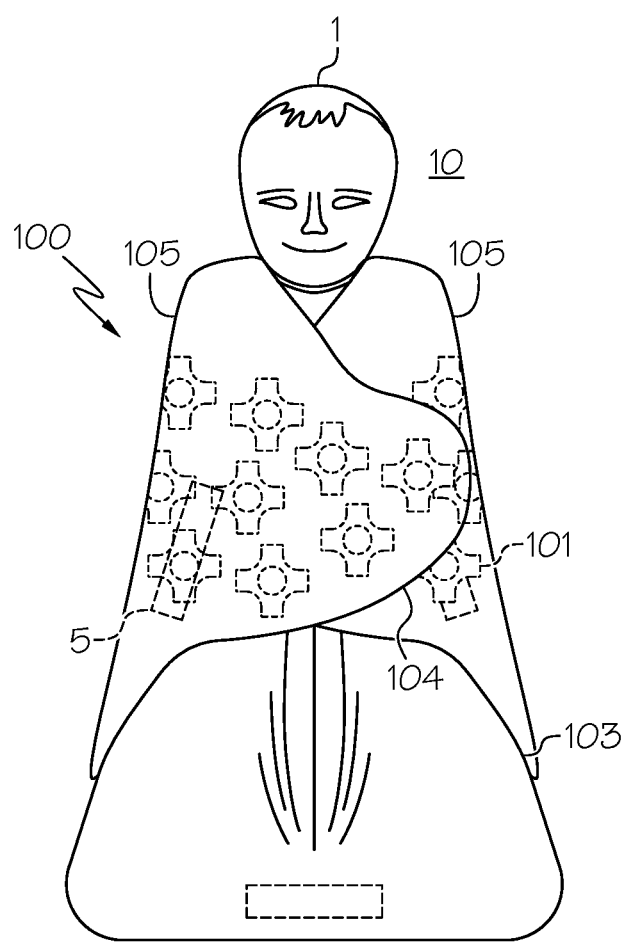
FIG. 1B schematically depicts a swaddle child soothing device with closed flaps, according to one or more embodiments shown and described herein.
Figure 1C:
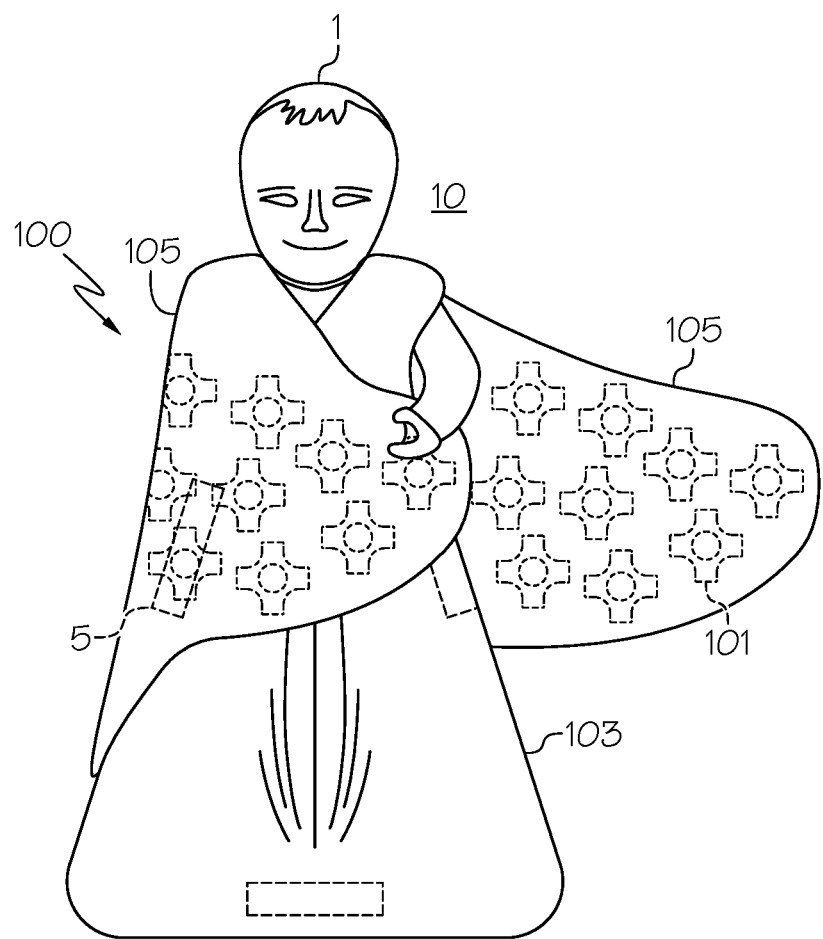
FIG. 1C schematically depicts a swaddle child soothing device with one open flap, according to one or more embodiments shown and described herein.

Embodiments described herein are directed to child soothing devices that include one or more artificial muscles configured to apply a selective pressure to a baby. The child soothing devices described herein include a swaddle, pillow, sleep slack, mattress, or the like, using a periodicity parameter to determine a rate of actuation and de-actuation of the one or more artificial muscles to simulate a heartbeat. The child soothing devices described herein include an inner layer, an outer layer, and one or more artificial muscles disposed in a cavity between the inner layer and the outer layer that are actuatable to selectively raise and lower a region of the artificial muscles to provide a selective, on demand inflated expandable fluid region. In particular, the one or more artificial muscles each include an electrode pair that may be drawn together by application of a voltage, thereby pushing dielectric fluid into the expandable fluid region, which applies localized pressure to the baby. Embodiments described herein are further directed to one or more warming elements to provide warmth to a baby. Various embodiments of the child soothing device and warming element, along with and the operation of each, are described in more detail herein. Whenever possible, the same reference numerals will be used throughout the drawings to refer to the same or like parts.

Referring now to FIGS. 1A-4B and 6A-6C, a child soothing device 10 is schematically depicted. In FIGS. 1A-1C, embodiments of the child soothing device 10 are depicted as a baby swaddle 100 having a central portion 103 and two flaps 105, although any suitable number of flaps 105 may be utilized in other embodiments. Within the central portion 103 and/or the two flaps 105, a soothing structure may comprise an outer layer and an inner layer, as discussed in more detail herein. The baby swaddle 100 is one exemplary type of wearable soothing structure. One or both flaps 105 may wrap around the central portion 103 in a way to provide a calming effect to a baby 1, which may experience a "startle reflex" caused by their own sudden arm movements. In FIG. 1A, the baby 1 is not swaddled. By keeping both of the baby's arm's gently restrained in the swaddle 100 (FIG. 1B) or at least keeping one of the baby's arms swaddled (FIG. 1C), the baby 1 can experience a greater sense of calm and/or security. The central portion 103 of the swaddle 100 may be opened/closed by any suitable mechanism/fastener, such as by way of non-limiting example buttons, snaps, zippers, fabric hook and loop fastener, and the like. The central portion 103 and/or flaps 105 may be made of any suitable material, which in some embodiments may feature a suitable amount of flexibility (cotton, polyester, blends, and the like). The swaddle 100 may utilize any number of artificial muscles 101 and/or warming elements 5 in the central portion 103 and/or flaps 105 in any suitable configuration, which in some embodiments may include overlap of one or more artificial muscles 101 with one or more warming elements 5. Any suitable type of warming element 5 may be utilized such as an insulated wire, carbon fiber, and the like. As described herein, actuation of the one or more artificial muscles 101 may be used to apply appropriate pressure to the baby 1 to create a feeling of held by a caregiver, which may also be done in conjunction with warming elements 5 that can simulate the warmth of a caregiver. As further described herein, actuation/de-actuation of one or more artificial muscles 101 may be utilized to simulate the heartbeat of a caregiver. While all artificial muscles 101 may actuate/de-actuate in unison in this embodiment, in other embodiments not all artificial muscles 101 may actuate/de-actuate together.

Figure 2A:
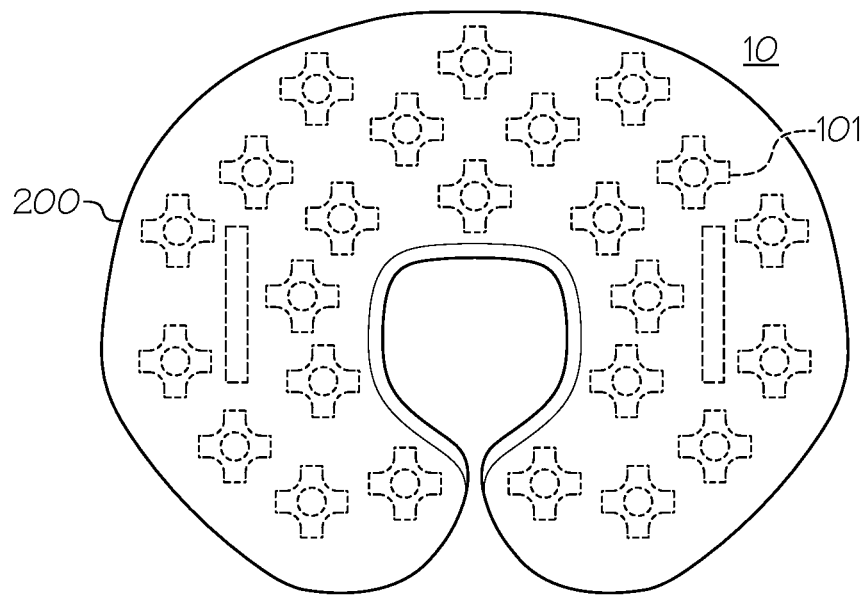
FIG. 2A schematically depicts a pillow child soothing device, according to one or more embodiments shown and described herein.
Figure 2B:
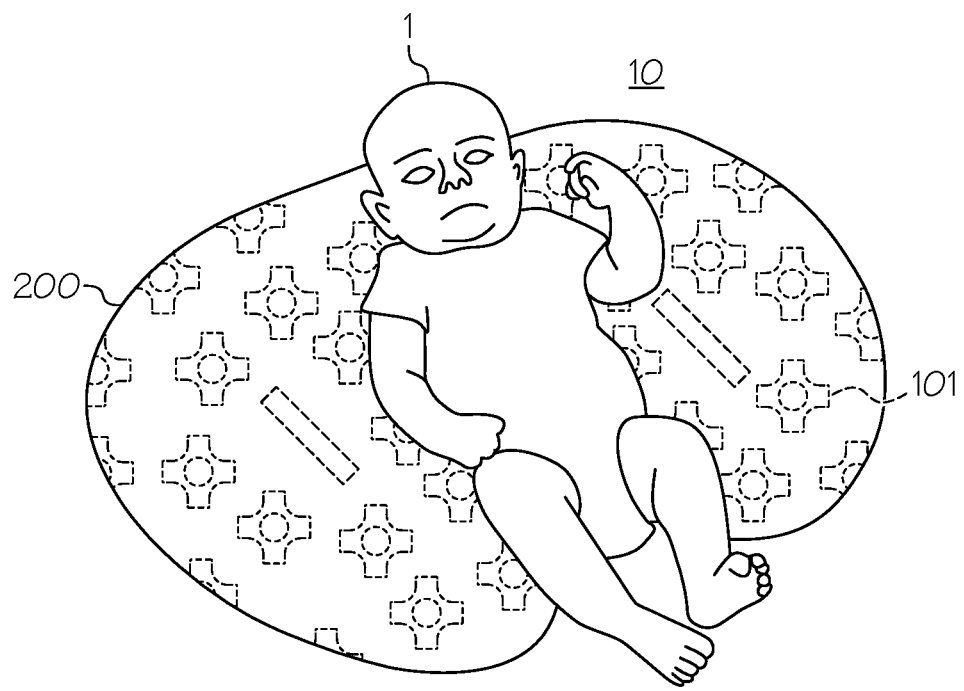
FIG. 2B schematically depicts a pillow child soothing device with a baby resting thereon, according to one or more embodiments shown and described herein.

Referring to FIGS. 2A-2B, the child soothing device 10 in this embodiment is a nursing pillow 200, although any suitable type of pillow may be utilized. The nursing pillow 200 is one exemplary type of supportive soothing structure. As depicted in FIG. 5A, two warming elements 5 are provided and numerous artificial muscles 101 are spread across the nursing pillow 200, although any number of artificial muscles 101 and/or warming elements 5 may be utilized in any suitable configuration. In FIG. 2B, the baby 1 is shown in a typical position where the gentle pressure of the artificial muscles 101 and/or warmth from the warming elements 5 can be felt. As discussed above with respect to the swaddle 100 embodiment, any suitable materials may be utilized in the nursing pillow 200.

Figure 3A:
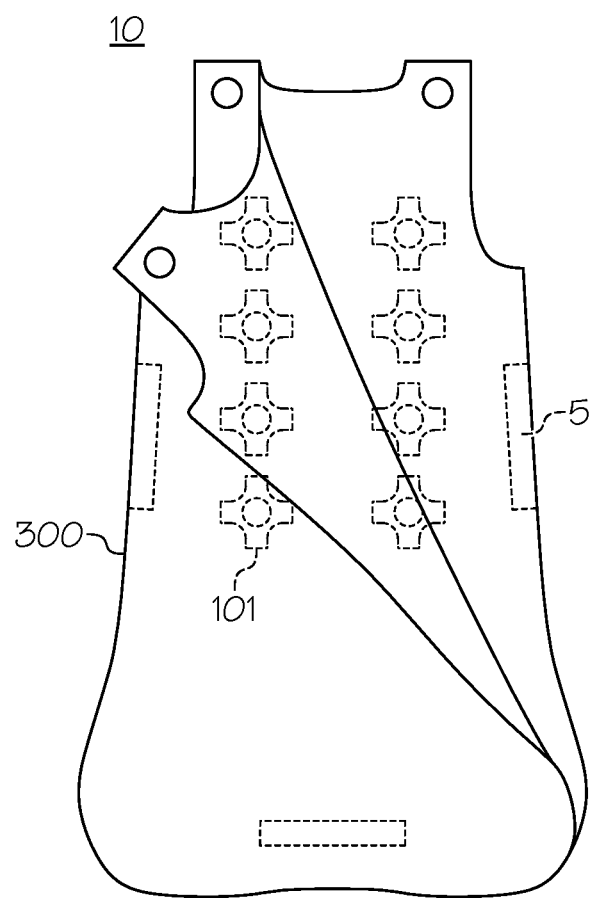
FIG. 3A schematically depicts a sleep sack child soothing device, according to one or more embodiments shown and described herein.
Figure 3B:
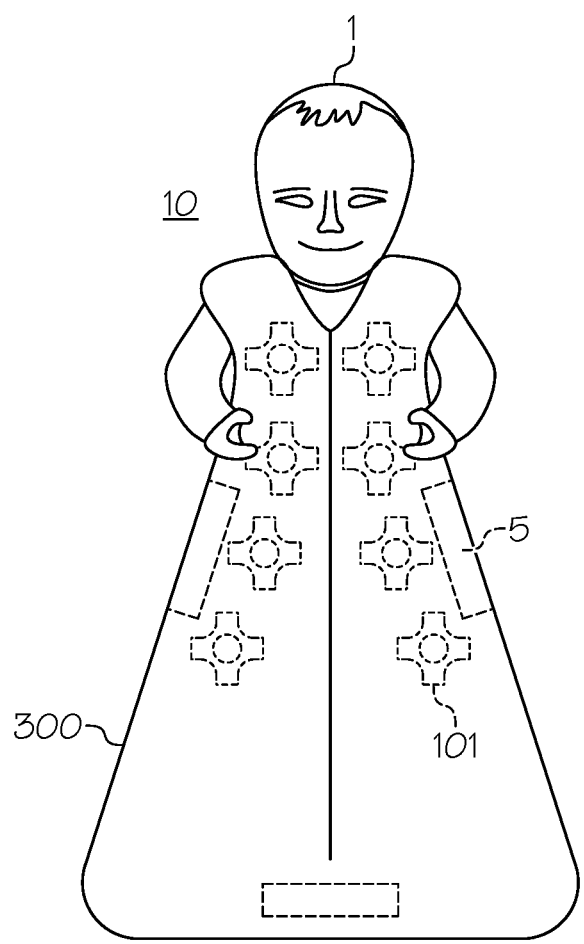
FIG. 3B schematically depicts a sleep sack child soothing with a baby therein, according to one or more embodiments shown and described herein.

Referring to FIGS. 3A-3B, the child soothing device 10 in this embodiment is a sleep sack 300, which is another exemplary type of wearable soothing structure. As depicted in FIG. 3A, two warming elements 5 are provided and numerous artificial muscles 101 are spread across the sleep sack 300, although any number of artificial muscles 101 and/or warming elements 5 may be utilized in any suitable configuration. While snaps are depicted to in FIG. 3A to close the sleep sack 300, any suitable configuration utilizing any suitable open/close mechanism may be utilized, as previously discussed for other embodiments. In FIG. 3B, the baby 1 is shown in a position where the gentle pressure of the artificial muscles 101 and/or warmth from the warming elements 5 can be felt. As discussed with respect to other embodiments, any suitable materials may be utilized in the sleep sack 300.

Figure 4A:
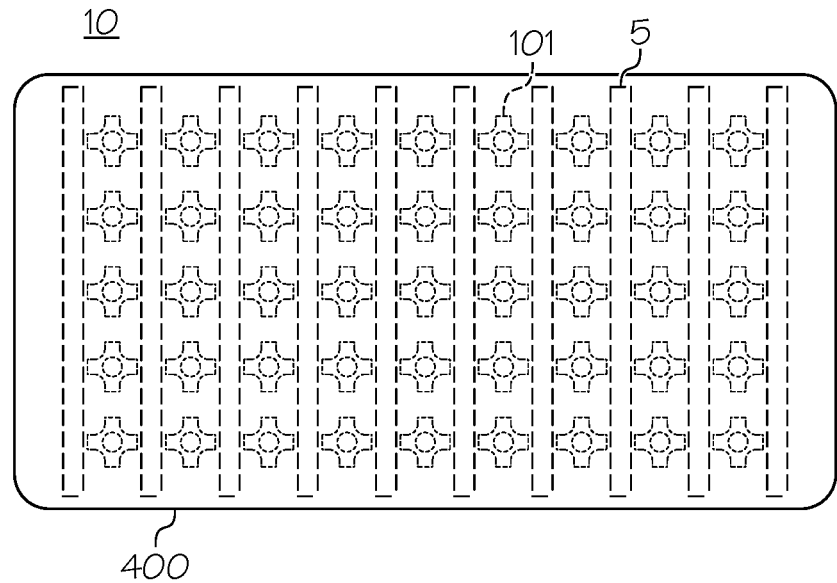
FIG. 4A schematically depicts a mattress child soothing device, according to one or more embodiments shown and described herein.
Figure 4B:
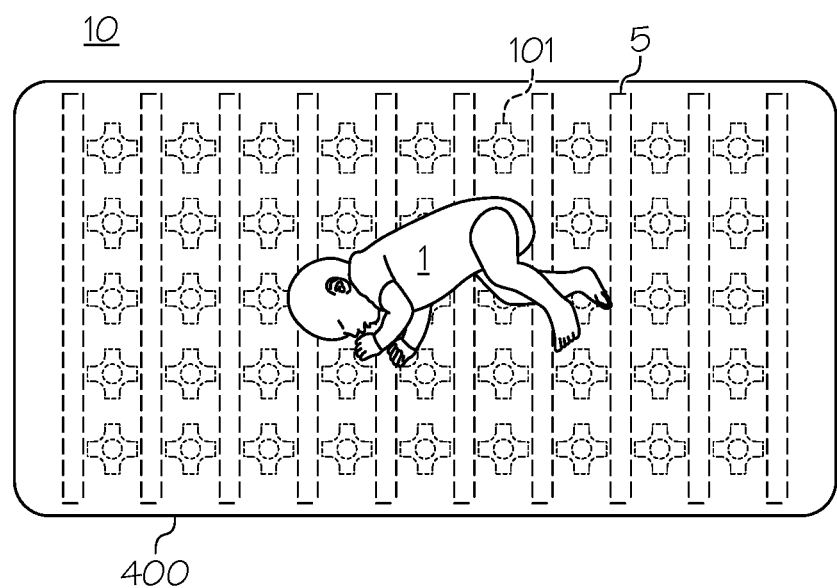
FIG. 4B schematically depicts a mattress child soothing with a baby resting thereon, according to one or more embodiments shown and described herein.

Referring to FIGS. 4A-4B, the child soothing device 10 in this embodiment is a mattress 400, which is another exemplary type of supportive soothing structure. As depicted in FIG. 4A, numerous warming elements 5 and artificial muscles 101 are spread across the mattress 400, although any number of artificial muscles 101 and/or warming elements 5 may be utilized in any suitable configuration. Any suitable type of mattress 400 (spring/coil, memory foam, gel, and the like) may be utilized. In FIG. 4B, the baby 1 is shown in a position where the gentle pressure of the artificial muscles 101 and/or warmth from the warming elements 5 can be felt. As discussed with respect to other embodiments, any suitable materials may be utilized in the mattress 400.

Figure 5:
FIG. 5 schematically depicts a user wearing a sensor device and utilizing a handheld device, according to one or more embodiments shown and described herein.

Referring to FIG. 5, a user 500 is depicted wearing a sensor device 502 and utilizing a handheld user device 504, each of which may comprise computing hardware such a processor(s), memory, communication hardware, and the like. In this embodiment, the sensor device 502 is a wearable device that detects the heartbeat and/or temperature of the user 500, although any suitable type of data may be utilized. As discussed further below, the sensor device 502 can provide heartbeat and/or temperature data to the child soothing device 10. For example, the heartbeat of the user 500 obtained by the sensor device 502 may be reproduced by actuation/de-actuation of artificial muscles 101 in the child soothing device 10 to reproduce the heartbeat of the user 500 (a parent, for example) for the baby 1. Similarly, temperature data obtained from the user 500 by the sensor device 502 may be utilized to adjust the warmth of generated by warming elements 5 in the child soothing device 10. Although depicted as a wrist-worn device, any suitable device capable of measuring the heartbeat and/or temperature of a user 500 may be utilized.

The user device 504 may be any suitable type of device capable of accepting user input, whether portable or stationary, such as a smartphone, tablet, laptop, wearable computer, desktop, server, and the like. The user device may receive, for example, input from the user 500 via a graphical user interface to actuate and/or de-actuate artificial muscles 101 (or more generally the child soothing device 10), to activate/deactivate warming elements 5, and/or to synchronize/desynchronize the child soothing device 10 to/from the heartbeat and/or temperature of the user 500. In some embodiments, the user 500 may specify a periodicity parameter value to simulate a heartbeat, be able to turn on/off warming elements 5, manage operation of the warming elements 5, and/or provide a specific amount of warmth (or a specific temperature) via the warming elements 5.

Figure 6A:
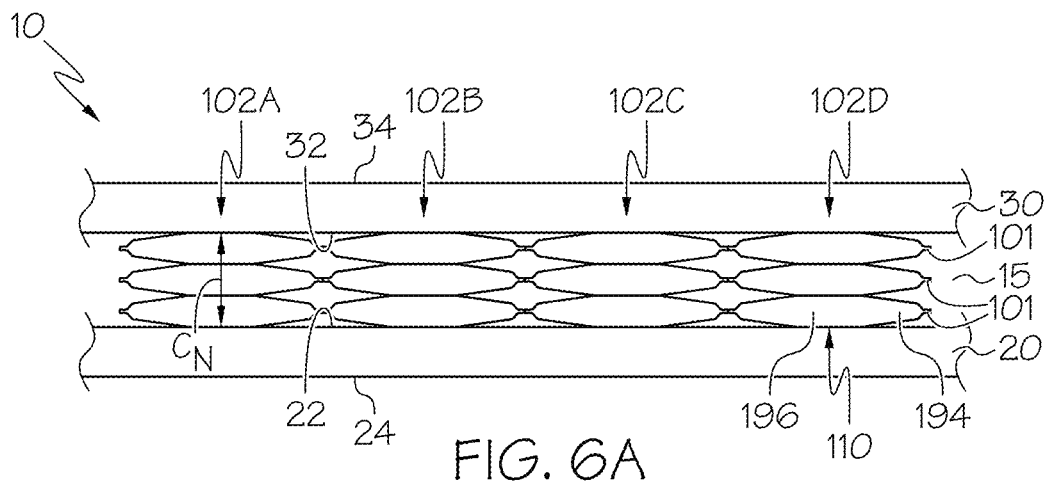
FIG. 6A schematically depicts a cross section of the child soothing device of FIGS. 1A-4B showing four stacks of artificial muscles of the child soothing device in a non-actuated state, according to one or more embodiments shown and described herein.
Figure 6B:
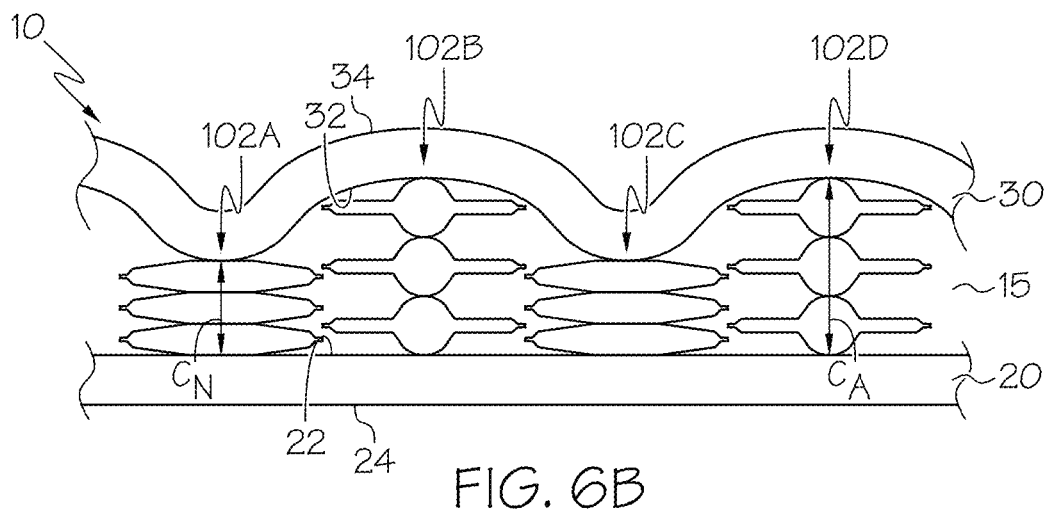
FIG. 6B schematically depicts a cross section of an embodiment of the child soothing device of FIG. 6A showing the four stacks of artificial muscles of the child soothing device in differing states of actuation, according to one or more embodiments shown and described herein.
Figure 6C:
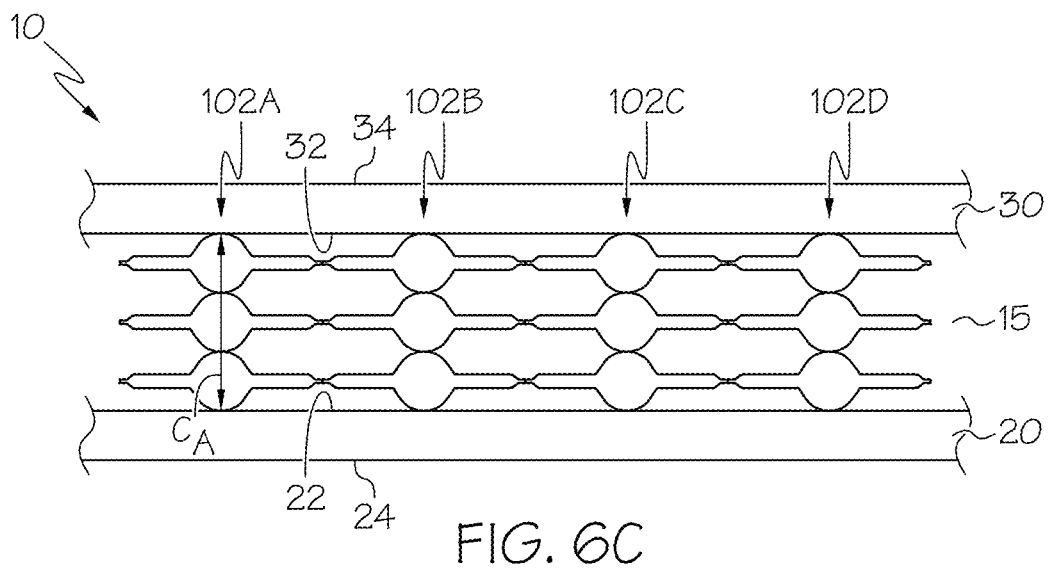
FIG. 6C schematically depicts a cross section of the child soothing device of FIG. 6A showing the four stacks of artificial muscles of the child soothing device in an actuated state, according to one or more embodiments shown and described herein.

Referring to FIGS. 6A-6C, the child soothing device 10 may include a soothing structure that includes an outer layer 20, an inner layer 30, and a cavity 15 disposed between the outer layer 20 and the inner layer 30. The child soothing device 10 also includes one or more artificial muscles 101 disposed between the inner layer 30 and the outer layer 20 of the child soothing device 10, for example, in the cavity 15. A schematic cross-section of the child soothing device 10 is shown in various states of actuation. In the embodiments depicted in FIGS. 6A-6C, each artificial muscle 101 is one of a plurality of artificial muscles 101. In particular, the plurality of artificial muscles 101 in FIGS. 6A-6C are arranged in a plurality of artificial muscle stacks 102. Moreover, embodiments are contemplated with a plurality of artificial muscles 101 arranged in a single layer within the cavity 15, in contrast to the artificial muscle stacks 102 of FIGS. 6A-6C. In operation, the one or more artificial muscles 101 are actuatable to expand and apply a pressure to the inner layer 30 of the child soothing device 10. As babies are not simple and uniform shapes, actuation of each artificial muscle 101 of the plurality of artificial muscles 101 may be independent and selective to maintain a consistent periodic actuation pressure on the baby 1 (in the swaddle 100 or sleep sack 300 embodiments, by way of non-limiting examples). In operation, actuation of the one or more artificial muscles 101 may be controlled by an actuation system 1400, which, as described in more detail with respect to FIG. 14, may include components housed in an onboard control unit 40 coupled to (or contained within) the child soothing device 10. This may include, for example, utilizing a pressure value (Pa/pascal, PSI, etc.) to determine the actuation amount of the one or more artificial muscles 101.

The inner layer 30 comprises an inner surface 32 facing the cavity 15 and an outer surface 34. The inner surface 32 may contact at least one artificial muscle 101 and, when worn, the outer surface 34 may contact the baby 1. The outer layer 20 comprises an inner surface 22 facing the cavity 15 and an outer surface 24 facing outward from the child soothing device 10. The inner surface 22 of the outer layer 20 may contact at least one artificial muscle 101. The inner layer 30 comprises an elastic material such that, when worn, the inner layer 30 may conform to the contours of the baby 1. In one embodiment, the outer layer 20 comprises a more rigid material than the inner layer 30, such as a rigid plastic or polymeric material, such that when the one or more artificial muscles 101 are actuated and press against both the inner layer 30 and the outer layer 20, the inner layer 30 deforms a greater degree than the outer layer 20 (indeed, the outer layer 20 may not deform at all) such that pressure is applied to the baby 1. As the outer layer 20 is more rigid than the inner layer 30, the outer layer 20 comprises a higher Young's modulus than the inner layer 30. In other embodiments, the outer layer 20 utilizes a less or equally rigid material in comparison to the inner layer 30.

Referring again to FIGS. 6A-6C, the plurality of artificial muscles 101 are arranged in a plurality of artificial muscles stacks 102. FIGS. 6A-6C depict an embodiment having four artificial muscle stacks 102A-102D in both a non-actuated state (FIGS. 6A and 6B) and an actuated state (FIGS. 6B and 6C) While these illustrative embodiments comprise four artificial muscle stacks 102A-102D, it should be understood that any number of artificial muscles stacks 102 are contemplated. In some embodiments (such as the swaddle 100), the plurality of artificial muscles 101 may be arranged uniformly between the inner layer 30 and the outer layer 20, encircling the inner layer 30 in a uniform radial array at one or multiple lengthwise positions along the length of the flaps 105. In some embodiments, the expandable fluid region 196 of each artificial muscle 101 of each of the plurality of artificial muscle stacks 102 are coaxially aligned with one another. However, in other embodiments, there may be some offset between the expandable fluid region 196 at least some of the artificial muscles 101 of the plurality of artificial muscles stacks 102. Moreover, while FIG. 6A-6C depict a plurality of artificial muscle stacks 102, embodiments are contemplated in which the plurality of artificial muscles 101 are arranged in a single layer within the cavity 15. This single layer may comprise a radial array of artificial muscles 101 encircling the inner layer 30 (uniformly or non-uniformly) at one or multiple lengthwise positions along the length of the flaps 105 in the swaddle 100 embodiment, by way of non-limiting example.

The one or more artificial muscles 101 each include an electrode pair 104 disposed in a housing 110 together with a dielectric fluid 198 (FIGS. 8-13). The electrode pair 104 is disposed in an electrode region 194 of the housing 110, adjacent an expandable fluid region 196. In operation, voltage may be applied to the electrode pair 104, drawing the electrode pair 104 together, which directs dielectric fluid into the expandable fluid region 196, expanding the expandable fluid region 196. In FIGS. 6A and 6B, one or more artificial muscles 101 are each in a non-actuated state. When the plurality of artificial muscles 101 are not actuated, the cavity 15 comprises a non-actuated thickness $C_N$. When the plurality of artificial muscles 101 are actuated, the cavity 15 comprises an actuated thickness $C_A$. As actuation of the plurality of artificial muscles 101 presses the inner layer 30 inward, the actuated thickness $C_A$ of the cavity 15 is larger than the non-actuated thickness $C_N$ of the cavity 15. In operation, when the baby 1 is wearing the swaddle 100 (for example), radial constriction of the inner layer 30 induced by the actuation of the one or more artificial muscles 101 in the flaps 105 applying encircling pressure to the baby 1. While FIG. 6A shows complete non-actuated states of the cross section of the child soothing device 10, and complete actuated states of the cross section of the child soothing device 10 is depicted in FIG. 6C, it should be understood that each individual artificial muscle 101 and each individual artificial muscle stack 102 may be independently actuated to provide selective pressure to the baby 1, as depicted in FIG. 6B.

Referring again to FIGS. 6A-6C, in some embodiments, the outer layer 20 of the child soothing device 10 is adjustable to fit onto a variety of different baby sizes. This adjustability may be achieved by a variety of mechanical features, such as adjustable straps. The child soothing device 10 may be operable to apply selective pressure to the baby 1 by actuation of the one or more artificial muscles 101. To actuate the child soothing device 10, voltage may be selectively applied to the one or more artificial muscles 101, expanding the expandable fluid regions 196 of the actuated artificial muscles 101.

In some embodiments, each of the one or more artificial muscles 101 are independently actuatable to apply selective pressure to the inner layer 30 of the child soothing device 10, which, when worn, applies selective pressure to the baby 1. In embodiments comprising the plurality of artificial muscle stacks 102, each artificial muscle stack 102 may be independently actuatable. Moreover, the artificial muscles 101 of a single artificial muscle stack 102 may also be independently actuatable, allowing the displacement stoke applied by a single artificial muscle stack 102 to be altered based on the number of individual artificial muscles 101 of the single artificial muscle stack 102 that are actuated. This facilitates an amount of pressure applied to the child soothing device 10. For example, a first artificial muscle stack may be actuated to increase the pressure exerted by a child soothing device 10, while a second artificial muscle stack may not be actuated, or actuated to a lesser extent, based upon the amount of pressure needed at a given time. If further pressure becomes necessary, the second artificial muscle stack can be actuated further.

Figure 7:
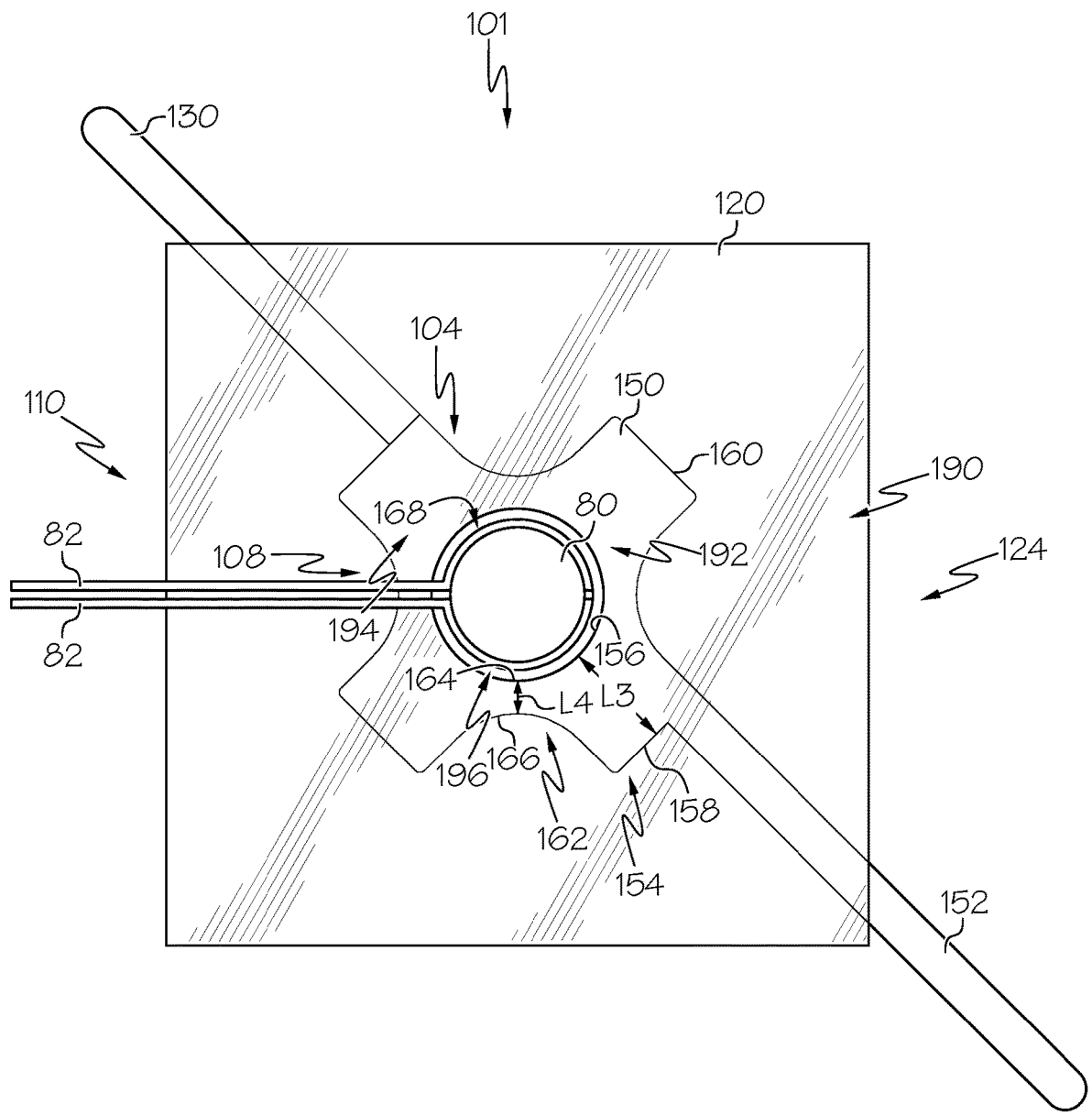
FIG. 7 schematically depicts a top view of an illustrative artificial muscle of the child soothing device of FIGS. 1A-4B with a pressure sensor affixed thereon, according to one or more embodiments shown and described herein.
Figure 8:
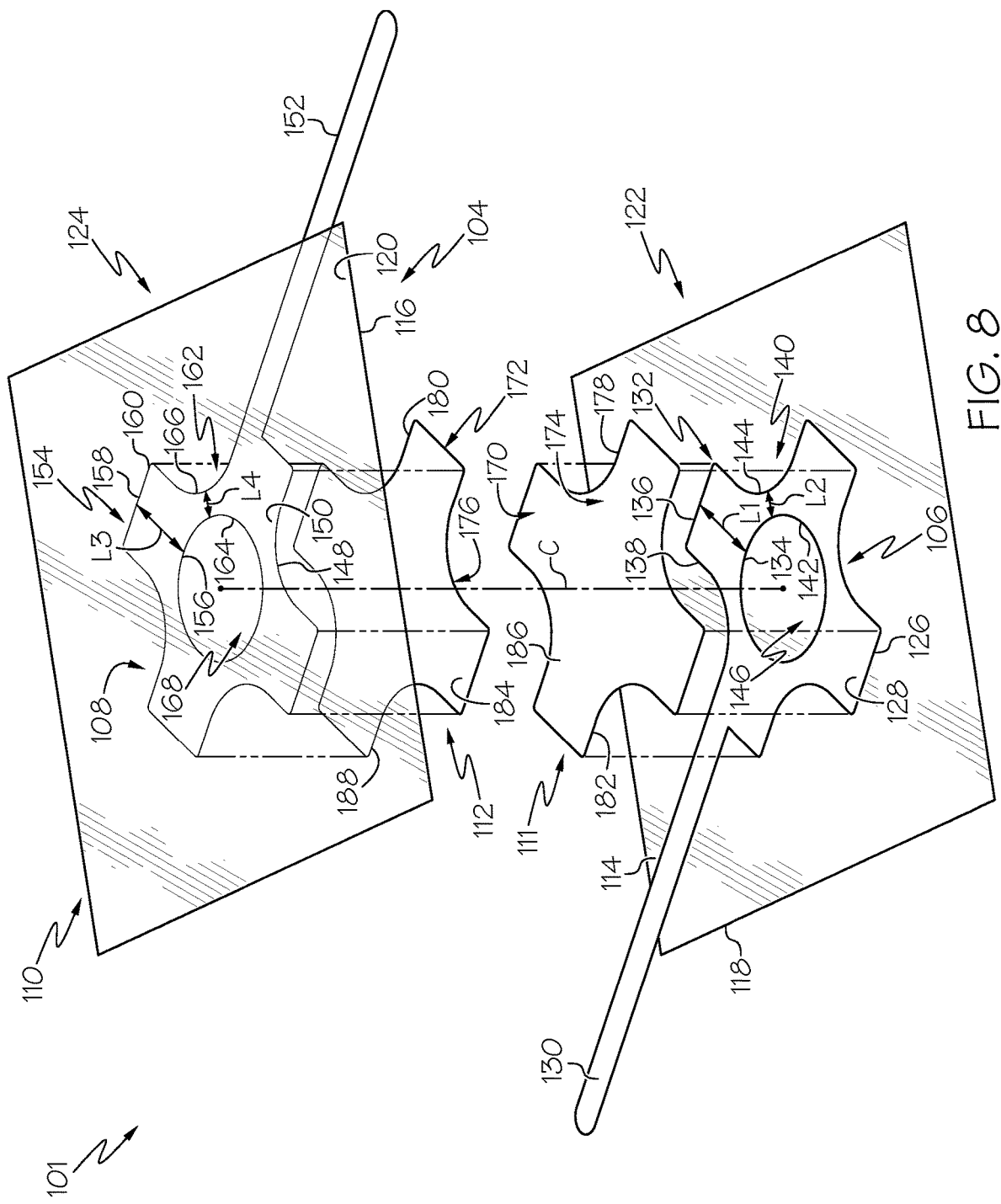
FIG. 8 schematically depicts an exploded view of the artificial muscle of FIG. 3 without the pressure sensor affixed thereon, according to one or more embodiments shown and described herein.
Figure 9:
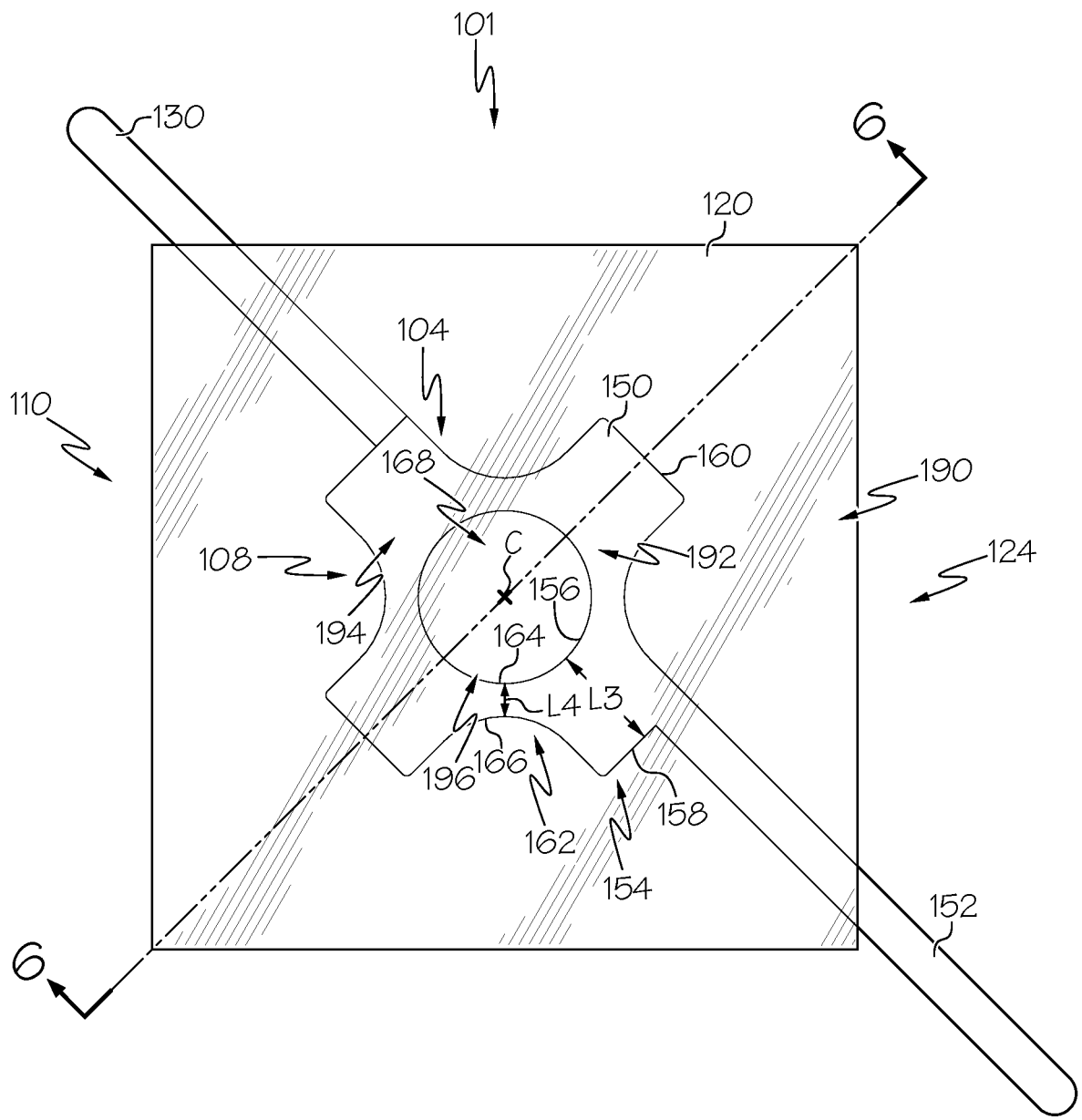
FIG. 9 schematically depicts a top view of the artificial muscle of FIG. 8, according to one or more embodiments shown and described herein.

Referring now to FIGS. 7-9, an example artificial muscle 101 of the child soothing device 10 is depicted in more detail. The artificial muscle 101 includes the housing 110, the electrode pair 104, including a first electrode 106 and a second electrode 108, fixed to opposite surfaces of the housing 110, a first electrical insulator layer 111 fixed to the first electrode 106, and a second electrical insulator layer 112 fixed to the second electrode 108. In some embodiments, the housing 110 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene.

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 101 is negatively charged.

Figure 14:
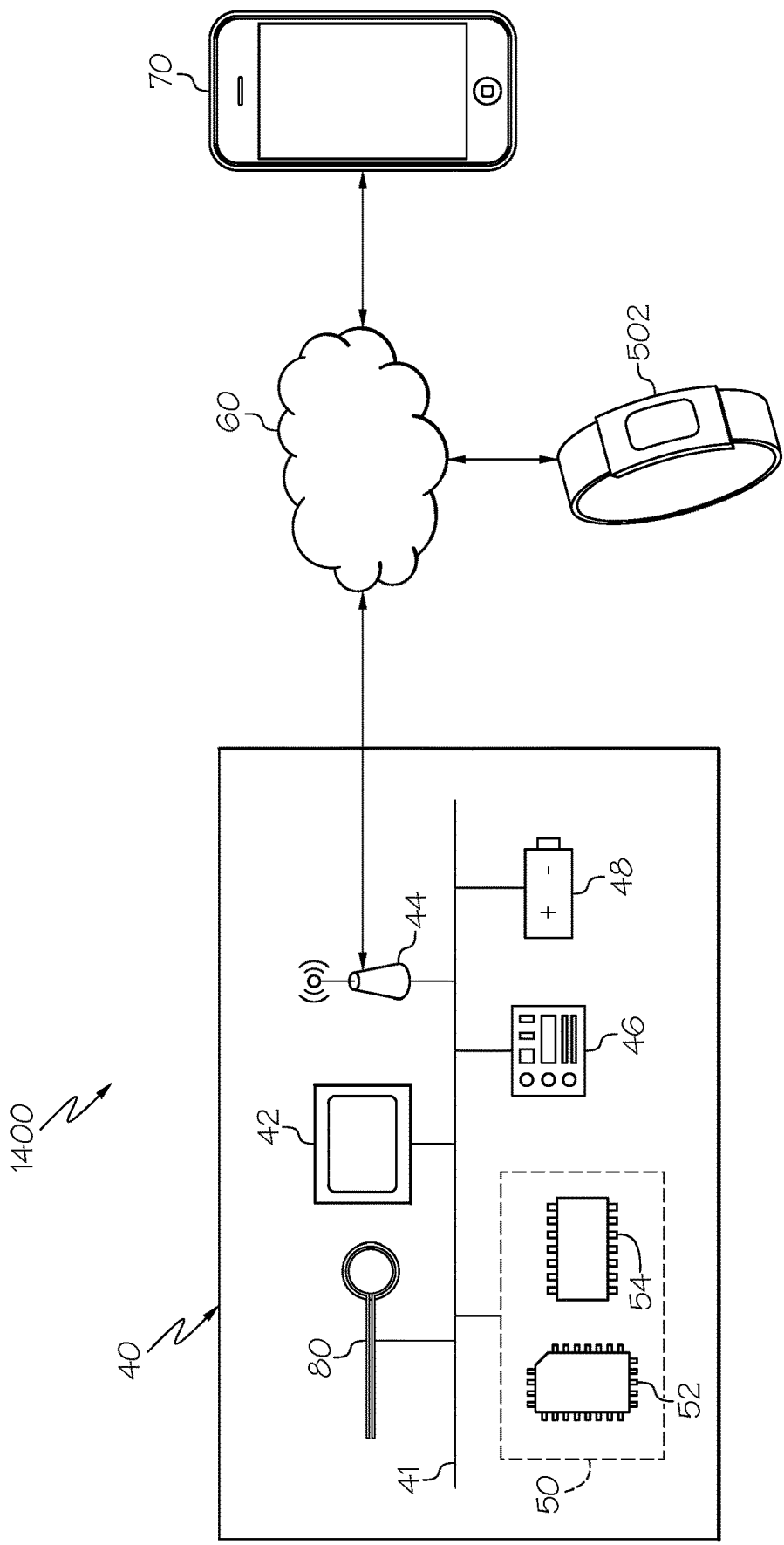
FIG. 14 schematically depicts an actuation system for operating the child soothing device of FIGS. 1A-4B, according to one or more embodiments shown and described herein.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the terminal is coupled, either directly or in series, to a power supply and a controller of an actuation system 1400, as shown in FIG. 14. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 1400 to actuate the second electrode 108.

The first electrode 106 includes two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140. In some embodiments, the bridge length L2 is 20% to 50% of the tab length L1, such as 30% to 40% of the tab length L1.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 may include only two tab portions 132 positioned on opposite sides or ends of the first electrode 106. In some embodiments, as shown in FIGS. 7-9, the first electrode 106 includes four tab portions 132 and four bridge portions 140 interconnecting adjacent tab portions 132. In this embodiment, the four tab portion 132 are arranged as two pairs of tab portions 132 diametrically opposed to one another. Furthermore, as shown, the first terminal 130 extends from the second end 136 of one of the tab portions 132 and is integrally formed therewith.

Like the first electrode 106, the second electrode 108 includes at least a pair of tab portions 154 and two or more bridge portions 162. Each bridge portion 162 is positioned between adjacent tab portions 154, interconnecting these adjacent tab portions 154. Each tab portion 154 has a first end 156 extending radially from a center axis C of the second electrode 108 to an opposite second end 158 of the tab portion 154, where the second end 158 defines a portion of an outer perimeter 160 of the second electrode 108. Due to the first electrode 106 and the second electrode 108 being coaxial with one another, the center axis C of the first electrode 106 and the second electrode 108 are the same. Each bridge portion 162 has a first end 164 extending radially from the center axis C of the second electrode to an opposite second end 166 of the bridge portion 162 defining another portion of the outer perimeter 160 of the second electrode 108. Each tab portion 154 has a tab length L3 and each bridge portion 162 has a bridge length L4 extending in a radial direction from the center axis C of the second electrode 108. The tab length L3 is a distance from the first end 156 to the second end 158 of the tab portion 154 and the bridge length L4 is a distance from the first end 164 to the second end 166 of the bridge portion 162. The tab length L3 is longer than the bridge length L4 of each bridge portion 162. In some embodiments, the bridge length L4 is 20% to 50% of the tab length L3, such as 30% to 40% of the tab length L3.

In some embodiments, the two or more tab portions 154 are arranged in one or more pairs of tab portions 154. Each pair of tab portions 154 includes two tab portions 154 arranged diametrically opposed to one another. In some embodiments, the second electrode 108 may include only two tab portions 154 positioned on opposite sides or ends of the first electrode 106. In some embodiments, as shown in FIGS. 7-9, the second electrode 108 includes four tab portions 154 and four bridge portions 162 interconnecting adjacent tab portions 154. In this embodiment, the four tab portions 154 are arranged as two pairs of tab portions 154 diametrically opposed to one another. Furthermore, as shown, the second terminal 152 extends from the second end 158 of one of the tab portions 154 and is integrally formed therewith.

Figure 10:
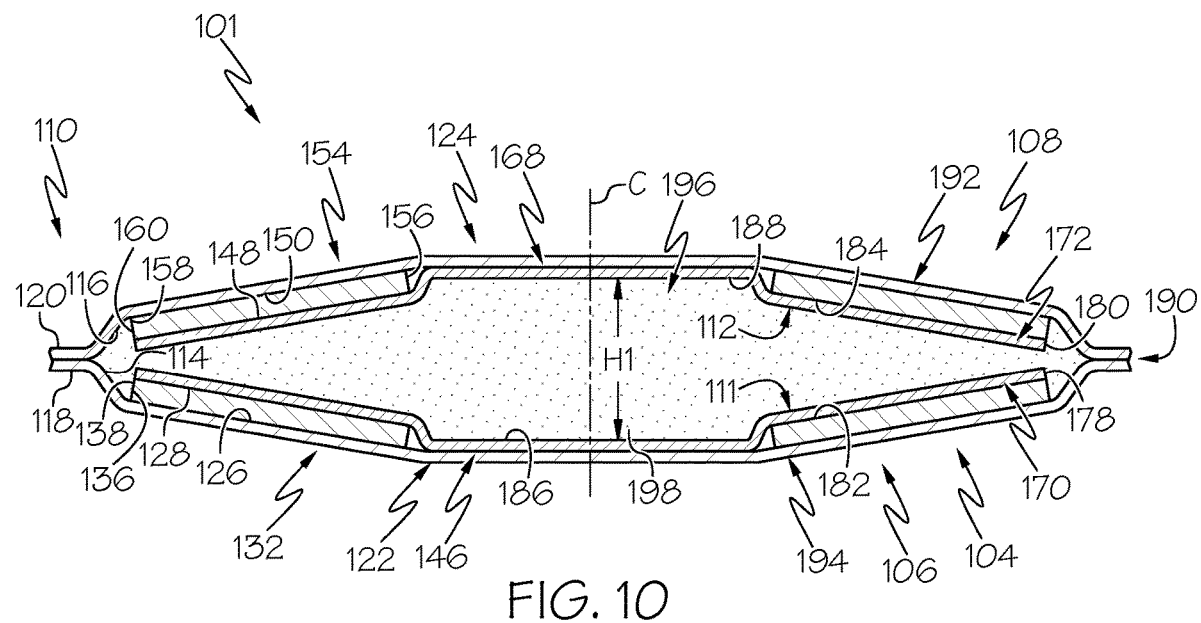
FIG. 10 schematically depicts a cross-sectional view of the artificial muscle of FIG. 8 taken along line 6-6 in FIG. 8 in a non-actuated state, according to one or more embodiments shown and described herein.
Figure 11:
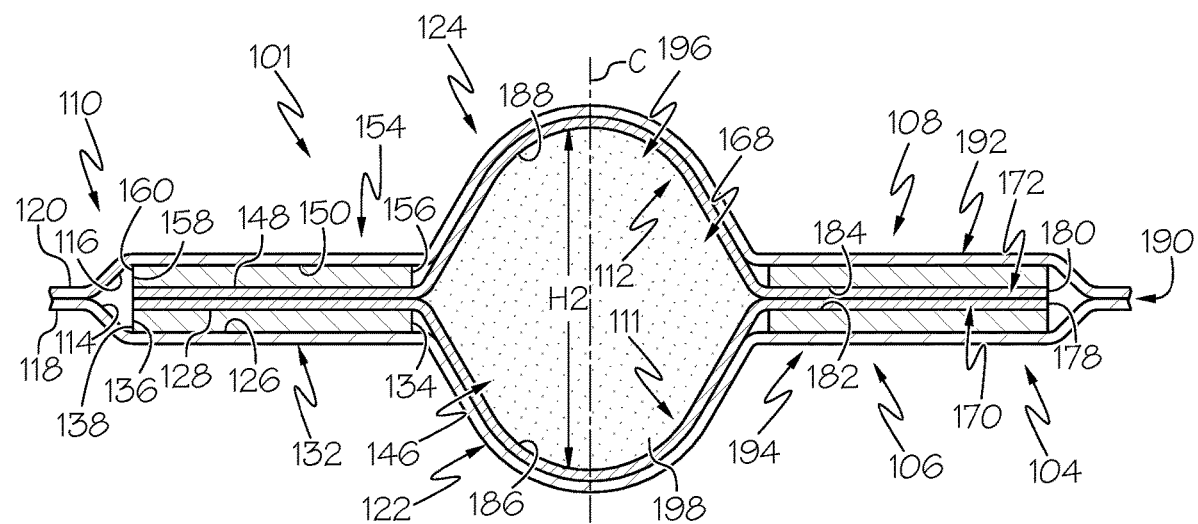
FIG. 11 schematically depicts a cross-sectional view of the artificial muscle of FIG. 8 taken along line 6-6 in FIG. 8 in an actuated state, according to one or more embodiments shown and described herein.
Figure 12:
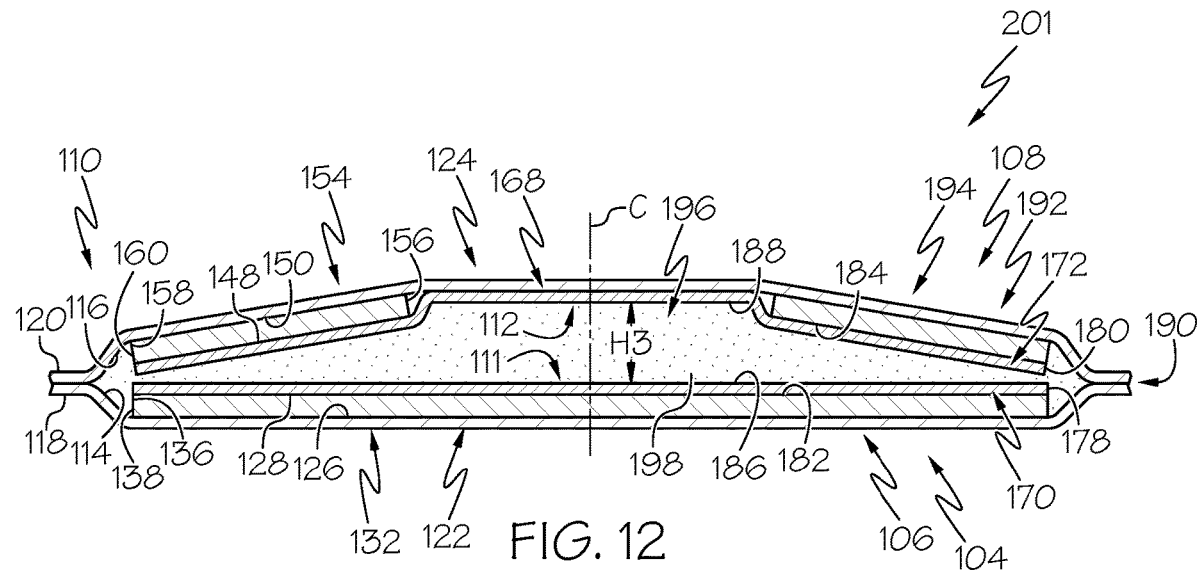
FIG. 12 schematically depicts a cross-sectional view of another illustrative artificial muscle in a non-actuated state, according to one or more embodiments shown and described herein.
Figure 13:
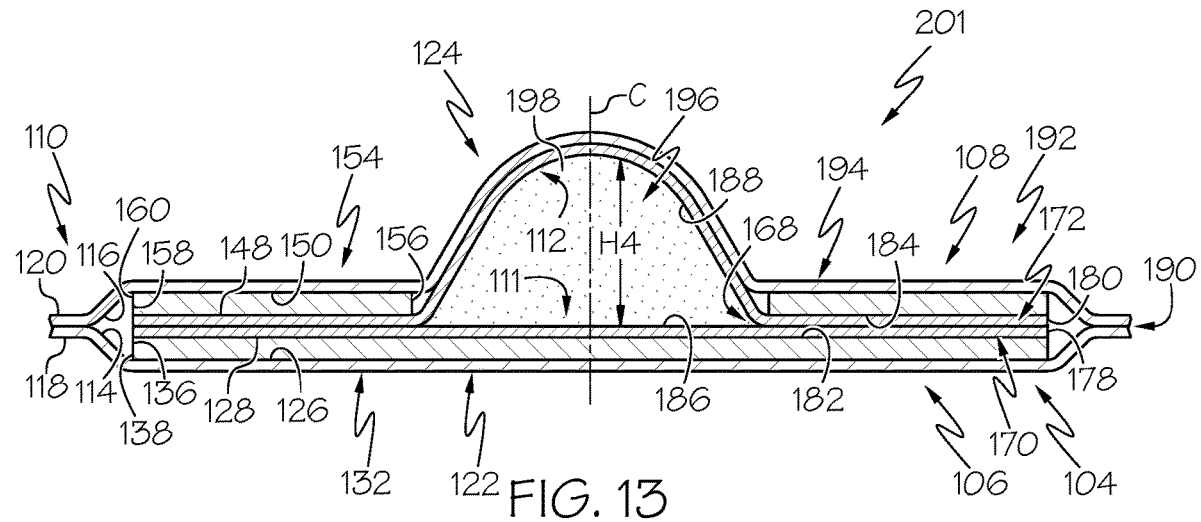
FIG. 13 schematically depicts a cross-sectional view of the artificial muscle of FIG. 8 in an actuated state, according to one or more embodiments shown and described herein.

Referring now to FIGS. 7-13, at least one of the first electrode 106 and the second electrode 108 has a central opening formed therein between the first end 134 of the tab portions 132 and the first end 142 of the bridge portions 140. In FIGS. 10 and 11, the first electrode 106 has a central opening 146. However, it should be understood that the first electrode 106 does not need to include the central opening 146 when a central opening is provided within the second electrode 108, as shown in FIGS. 12 and 13. Alternatively, the second electrode 108 does not need to include the central opening when the central opening 146 is provided within the first electrode 106. Referring to FIGS. 7-13, the first electrical insulator layer 111 and the second electrical insulator layer 112 have a geometry generally corresponding to the first electrode 106 and the second electrode 108, respectively. Thus, the first electrical insulator layer 111 and the second electrical insulator layer 112 each have tab portions 170, 172 and bridge portions 174, 176 corresponding to like portions on the first electrode 106 and the second electrode 108. Further, the first electrical insulator layer 111 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 111 and the second electrical insulator layer 112 generally include the same structure and composition. As such, in some embodiments, the first electrical insulator layer 111 and the second electrical insulator layer 112 each include an adhesive surface 182, 184 and an opposite non-sealable surface 186, 188, respectively. Thus, in some embodiments, the first electrical insulator layer 111 and the second electrical insulator layer 112 are each a polymer tape adhered to the inner surface 128 of the first electrode 106 and the inner surface 150 of the second electrode 108, respectively.

Referring again to FIGS. 7-13, the artificial muscle 101 is shown in its assembled form with the first terminal 130 of the first electrode 106 and the second terminal 152 of the second electrode 108 extending past an outer perimeter of the housing 110, i.e., the first film layer 122 and the second film layer 124. As shown in FIG. 8, the second electrode 108 is stacked on top of the first electrode 106 and, therefore, the first electrode 106, the first film layer 122, and the second film layer 124 are not shown. In its assembled form, the first electrode 106, the second electrode 108, the first electrical insulator layer 111, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like.

The first electrode 106, the second electrode 108, the first electrical insulator layer 111, and the second electrical insulator layer 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146, 168 of the first electrode 106 and the second electrode 108 form the expandable fluid region 196 and are arranged to be axially stacked on one another. Although not shown, the housing 110 may be cut to conform to the geometry of the electrode pair 104 and reduce the size of the artificial muscle 101, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 101 using a needle or other suitable injection device.

Referring now to FIGS. 10 and 11, the artificial muscle 101 is actuatable between a non-actuated state and an actuated state. In the non-actuated state, as shown in FIG. 6, the first electrode 106 and the second electrode 108 are partially spaced apart from one another proximate the central openings 146, 168 thereof and the first end 134, 156 of the tab portions 132, 154. The second end 136, 158 of the tab portions 132, 154 remain in position relative to one another due to the housing 110 being sealed at the outer perimeter 138 of the first electrode 106 and the outer perimeter 160 of the second electrode 108. In FIGS. 6A and 6B, at least one of the one or more artificial muscles 101 of the child soothing device 10 is in the non-actuated state. In the actuated state, as shown in FIG. 11, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196. In FIGS. 6B and 6C, at least one of the one or more artificial muscles 101 of the child soothing device 10 is in the actuated state.

Referring now to FIG. 10, the artificial muscle 101 is shown in the non-actuated state. The electrode pair 104 is provided within the electrode region 194 of the unsealed portion 192 of the housing 110. The central opening 146 of the first electrode 106 and the central opening 168 of the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the tab portions 132, 154 are brought into contact with one another. Thus, dielectric fluid 198 is provided between the first electrode 106 and the second electrode 108, thereby separating the first end 134, 156 of the tab portions 132, 154 proximate the expandable fluid region 196. Stated another way, a distance between the first end 134 of the tab portion 132 of the first electrode 106 and the first end 156 of the tab portion 154 of the second electrode 108 is greater than a distance between the second end 136 of the tab portion 132 of the first electrode 106 and the second end 158 of the tab portion 154 of the second electrode 108. This results in the electrode pair 104 zippering toward the expandable fluid region 196 when actuated. In some embodiments, the first electrode 106 and the second electrode 108 may be flexible. Thus, as shown in FIG. 8, the first electrode 106 and the second electrode 108 are convex such that the second ends 136, 158 of the tab portions 132, 154 thereof may remain close to one another, but spaced apart from one another proximate the central openings 146, 168. In the non-actuated state, the expandable fluid region 196 has a first height H1.

When actuated, as shown in FIG. 11, the first electrode 106 and the second electrode 108 zipper toward one another from the second ends 144, 158 of the tab portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply (such as power supply 48 of FIG. 14). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first electrical insulator layer 111 to deform in a first axial direction along the center axis C of the first electrode 106 and causes the second film layer 124 and the second electrical insulator layer 112 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments of the artificial muscle 101 disclosed herein, specifically, the tab portions 132, 154 with the interconnecting bridge portions 174, 176, provide a number of improvements over actuators that do not include the tab portions 132, 154, such as hydraulically amplified self-healing electrostatic (HA-SEL) actuators described in the paper titled "*Hydraulically amplified self-healing electrostatic actuators with muscle-like performance*" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 101 including two pairs of tab portions 132, 154 on each of the first electrode 106 and the second electrode 108, respectively, reduces the overall mass and thickness of the artificial muscle 101, reduces the amount of voltage required during actuation, and decreases the total volume of the artificial muscle 101 without reducing the amount of resulting force after actuation as compared to known HASEL actuators including donut-shaped electrodes having a uniform, radially-extending width. More particularly, the tab portions 132, 154 of the artificial muscle 101 provide zipping fronts that result in increased actuation power by providing localized and uniform hydraulic actuation of the artificial muscle 101 compared to HASEL actuators including donut-shaped electrodes. Specifically, one pair of tab portions 132, 154 provides twice the amount of actuator power per unit volume as compared to donut-shaped HASEL actuators, while two pairs of tab portions 132, 154 provide four times the amount of actuator power per unit volume. The bridge portions 174, 176 interconnecting the tab portions 132, 154 also limit buckling of the tab portions 132, 154 by maintaining the distance between adjacent tab portions 132, 154 during actuation. Because the bridge portions 174, 176 are integrally formed with the tab portions 132, 154, the bridge portions 174, 176 also prevent leakage between the tab portions 132, 154 by eliminating attachment locations that provide an increased risk of rupturing.

In operation, when the artificial muscle 101 is actuated by providing a voltage and applying the voltage to the electrode pair 104 of the artificial muscle 101, expansion of the expandable fluid region 196 produces a force of 3 Newton-millimeters (N.mm) per cubic centimeter ($cm^3$) of actuator volume or greater, such as 4 N.mm per $cm^3$ or greater, 5 N.mm per $cm^3$ or greater, 6 N.mm per $cm^3$ or greater, 7 N.mm per $cm^3$ or greater, 8 N.mm per $cm^3$ or greater, or the like. Providing the voltage may comprise generating the voltage, for example, in an embodiment in which the power supply 48 (FIG. 14) is a battery, converting the voltage, for example in embodiment in which the power supply 48 (FIG. 14) is a power adaptor, or any other known or yet to be developed technique for readying a voltage for application. In one example, when the artificial muscle 101 is actuated by a voltage of 9.5 kilovolts (kV), the artificial muscle 101 provides a resulting force of 5 N. In another example, when the artificial muscle 101 is actuated by a voltage of 10 kV the artificial muscle 101 provides 440% strain under a 500 gram load.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

As shown in FIGS. 12 and 13, another embodiment of an artificial muscle 201 is illustrated. The artificial muscle 201 is substantially similar to the artificial muscle 101. As such, like structure is indicated with like reference numerals. However, as shown, the first electrode 106 does not include a central opening. Thus, only the second electrode 108 includes the central opening 168 formed therein. As shown in FIG. 12, the artificial muscle 201 is in the non-actuated state with the first electrode 106 being planar and the second electrode 108 being convex relative to the first electrode 106. In the non-actuated state, the expandable fluid region 196 has a first height H3. In the actuated state, as shown in FIG. 13, the expandable fluid region 196 has a second height H4, which is greater than the first height H3. It should be appreciated that by providing the central opening 168 only in the second electrode 108 as opposed to both the first electrode 106 and the second electrode 108, the total deformation may be formed on one side of the artificial muscle 201. In addition, because the total deformation is formed on only one side of the artificial muscle 201, the second height H4 of the expandable fluid region 196 of the artificial muscle 201 extends further from a longitudinal axis perpendicular to the central axis C of the artificial muscle 201 than the second height H2 of the expandable fluid region 196 of the artificial muscle 101 when all other dimensions, orientations, and volume of dielectric fluid are the same. It should be understood that embodiments of the artificial muscle 201 may be used together with or in place of the one or more artificial muscles 101 of the child soothing device 10 of FIGS. 1A-4B and 6A-C.

In some embodiments, as shown in FIG. 7, a pressure sensor 80 may reside on the housing 110 and be aligned with the central opening 168 or central opening 146, which are openings in the first electrode 106 and second electrode 108, respectively. In some embodiments, the pressure sensor 80 may be disposed on the expandable fluid region 196 of the housing 110. In other embodiments, the pressure sensor 80 may be located on any suitable surface of the housing 110 or an artificial muscle 101. The pressure sensor 80 is utilized to measure pressure exerted in the child soothing device 10 to maintain proper pressure on a baby 1 within, for example, a swaddle 100 or a sleep sack 300.

In some embodiments, different pressure sensors 80 within the child soothing device 10 may be located at different locations with respect to different housings 110 and/or an artificial muscles 101. In this embodiment, the pressure sensor 80 has two sensor protrusions 82 that extend outwardly from the pressure sensor 80 and may be disposed between the inner layer 30 and outer layer 20. Sensor protrusions may be used, for example, to wirelessly communicate with other components, such as a controller 50 (as shown in FIG. 14) and/or other wireless sensors located on other artificial muscles 101. In other embodiments, any number of sensor protrusions 82 of any shape, size, and/or configuration may be utilized. In still other embodiments, the pressure sensor 80 may have no sensor protrusions 82.

In some embodiments, the pressure sensor 80 may be of any suitable type, such as, by way of non-limiting example, absolute, gauge, or differential pressure sensors. Sensing by the pressure sensor 80 may include any suitable technique such as resistive sensing, capacitive sensing, piezoelectric sensing, optical sensing, micro electro-mechanical system (MEMS), or any other suitable type of pressure sensing technique. Output from the pressure sensor 80 may be by millivolt-output transducers, volt-output transducers, transmitters, or any other suitable components.

Referring now to FIG. 14, an actuation system 1400 may be provided for operating the child soothing device 10, in particular, operate the one or more artificial muscles 101 of the child soothing device 10. The actuation system 1400 may comprise a controller 50, the one or more pressure sensors 80, an operating device 46, a power supply 48, a display device 42, network interface hardware 44, and a communication path 41 communicatively coupled these components, some or all of which may be disposed in the onboard control unit 40.

The controller 50 may comprise a processor 52 and a non-transitory electronic memory 54 to which various components are communicatively coupled. In some embodiments, the processor 52 and the non-transitory electronic memory 54 and/or the other components are included within a single device. In other embodiments, the processor 52 and the non-transitory electronic memory 54 and/or the other components may be distributed among multiple devices that are communicatively coupled. The controller 50 may include non-transitory electronic memory 54 that stores a set of machine-readable instructions. The processor 52 may execute the machine-readable instructions stored in the non-transitory electronic memory 54. The non-transitory electronic memory 54 may comprise RAM, ROM, flash memories, hard drives, or any device capable of storing machine-readable instructions such that the machine-readable instructions can be accessed by the processor 52. Accordingly, the actuation system 1400 described herein may be implemented in any computer programming language, as pre-programmed hardware elements, or as a combination of hardware and software components. The non-transitory electronic memory 54 may be implemented as one memory module or a plurality of memory modules. The controller 50 may receive a current periodic actuation pressure value from the pressure sensor 80, output an updated periodic actuation pressure value the pressure sensor 80, and/or modify actuation of at least one of the one or more artificial muscles based upon the updated periodic actuation pressure value to maintain the consistent amount of periodic actuation pressure. The artificial muscle may be one of a plurality of artificial muscles such that adjusting the actuation of each of the plurality of muscles maintains the consistent amount of periodic actuation pressure at inner layer 30. As discussed further with respect to FIG. 15, the consistent amount of periodic actuation pressure at an inner surface 32 of the inner layer 30 may be maintained based upon a feedback loop maintained by the controller 50 in coordination with one or more pressure sensors 80.

In some embodiments, the non-transitory electronic memory 54 includes instructions for executing the functions of the actuation system 1400. The instructions may include instructions for operating the child soothing device 10, for example, instructions for actuating the one or more artificial muscles 101, individually or collectively, and actuating the artificial muscles stacks, individually or collectively.

The processor 52 may be any device capable of executing machine-readable instructions. For example, the processor 52 may be an integrated circuit, a microchip, a computer, or any other computing device. The non-transitory electronic memory 54 and the processor 52 are coupled to the communication path 41 that provides signal interconnectivity between various components and/or modules of the actuation system 1400. Accordingly, the communication path 41 may communicatively couple any number of processors with one another, and allow the modules coupled to the communication path 41 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 14, the communication path 41 communicatively couples the processor 52 and the non-transitory electronic memory 54 of the controller 50 with a plurality of other components of the actuation system 1400. For example, the actuation system 1400 depicted in FIG. 14 includes the processor 52 and the non-transitory electronic memory 54 communicatively coupled with the pressure sensor 80, operating device 46, and the power supply 48.

The operating device 46 allows for a user to control operation of the artificial muscles 101 of the child soothing device 10. In some embodiments, the operating device 46 may be a switch, toggle, button, or any combination of controls to provide user operation. The operating device 46 is coupled to the communication path 41 such that the communication path 41 communicatively couples the operating device 46 to other modules of the actuation system 1400. The operating device 46 may provide a user interface for receiving user instructions as to a specific operating configuration of the warming element 5 and/or child soothing device 10, such as maintaining a desired temperature of the warming element 5 and/or a periodic actuation pressure value applied to a baby 2 in a swaddle 4 or sleep sack 300 or laying upon a pillow 200 or mattress 400.

The power supply 48 (e.g., battery) provides power to the one or more artificial muscles 101 of the child soothing device 10. In some embodiments, the power supply 48 is a rechargeable direct current power source. It is to be understood that the power supply 48 may be a single power supply or battery for providing power to the one or more artificial muscles 101 of the child soothing device 10. A power adapter (not shown) may be provided and electrically coupled via a wiring harness or the like for providing power to the one or more artificial muscles 101 of the child soothing device 10 via the power supply 48. Indeed, the power supply 48 is a device that can receive power at one level (e.g., one voltage, power level, or current) and output power at a second level (e.g., a second voltage, power level, or current).

In some embodiments, the actuation system 1400 also includes a display device 42. The display device 42 is coupled to the communication path 41 such that the communication path 41 communicatively couples the display device 42 to other modules of the actuation system 1400. The display device 42 may be located on the child soothing device 10, for example, as part of the onboard control unit 40, and may output a notification in response to an actuation state of the artificial muscles 101 of the child soothing device 10 or indication of a change in the actuation state of the one or more artificial muscles 101 of the child soothing device 10. In other embodiments, the display device 42 may be part of the user device 504 depicted in FIG. 5. The display device 42 may be a touchscreen that, in addition to providing optical information, detects the presence and location of a tactile input upon a surface of or adjacent to the display device 42. Accordingly, the display device 42 may include the operating device 46 and receive mechanical input directly upon the optical output provided by the display device 42. For example, the user 500 may be able to specify a desired periodic actuation pressure value.

In some embodiments, the actuation system 1400 includes network interface hardware 44 for communicatively coupling the actuation system 1400 to a portable device 70 and/or a sensor device 502 via a network 60. The portable device 70 may correspond in some embodiments to the user device 540 in FIG. 5. The portable device 70 may include, without limitation, a smartphone, a tablet, a personal media player, or any other electric device that includes wireless communication functionality. It is to be appreciated that, when provided, the portable device 70 may serve to provide user commands to the controller 50, instead of the operating device 46. As such, a user may be able to control or set a program for controlling the artificial muscles 101 of the child soothing device 10 utilizing the controls of the operating device 46. Thus, the artificial muscles 101 of the child soothing device 10 may be controlled remotely via the portable device 70 wirelessly communicating with the controller 50 via the network 60. For example, the user may be able to specify a desired pressure value. The portable device 70 may also receive and display pressure readings from one or more pressure sensors 80 associated with one or more of the artificial muscles 101.

In some embodiments, the sensor device 502 may be worn by a user 500 as depicted in FIG. 5. For example, the heartbeat or other biorhythm of the user 500 may be detected and transmitted to the onboard control unit 40. In this example, the heartbeat can then be utilized by a periodicity parameter to control the rate of actuation/de-actuation of the artificial muscles, as further discussed in FIG. 15. In some embodiments, the heartbeat may be continually monitored such that the periodicity parameter governing the rate artificial muscle actuation/de-actuation may be updated in real-time or periodically based upon updated readings of the user's heartbeat. In other embodiments, the heartbeat, once measured, may serve as an unchanging periodicity parameter value for the actuation/de-actuation of the artificial muscles.

Figure 15:
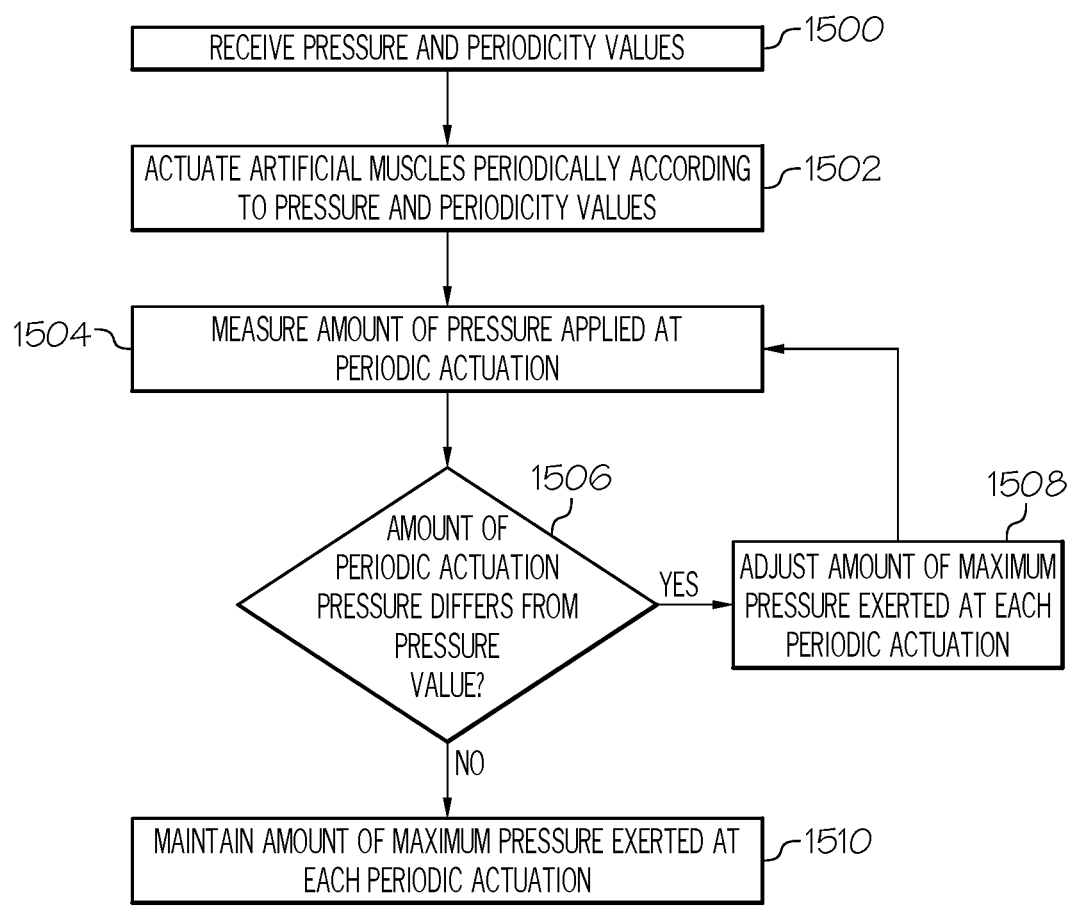
FIG. 15 schematically depicts a flowchart for maintaining consistent periodic actuation pressure applied by the child soothing device, according to one or more embodiments shown and described herein.

Referring now to FIG. 15, a flowchart depicts an exemplary method for the child soothing device to apply periodic pressure to a baby. At block 1500, a pressure value may be received at the controller (or any other suitable device) from a user device (such as a smartphone by way of non-limiting example), a pressure sensor located within the child soothing device, and/or any other suitable device. For example, a user wanting to maintain a certain maximum periodic pressure applied by the child soothing device waits as the pressure sensor measures the current exerted by the child soothing device at the peak values. A periodicity value may be received at the controller (or any other suitable device) from a user sensor or any other suitable device. For example, the periodicity value may correspond to the measured heartbeat of the user as detected by the user sensor, and the pressure value may be received from a user device.

At block 1502, one or more artificial muscles may be actuated such that the child soothing device applies pressure to a user such as a baby via a surface (such as a nursing pillow and/or mattress) or via a wrap-around (such as a swaddle and/or sleep sack). Continuing with this example, the user waits as the artificial muscles actuate, which increases pressure exerted by child soothing device at each full actuation (i.e., for each simulated heartbeat). At block 1504, one or more pressure sensors may measure an amount of pressure being applied to the baby at each periodic actuation via the child soothing device. Continuing with this example, after the artificial muscles have actuated exert the proper pressure at the peak periodic actuation pressure, updated pressure measurements may be taken. Specifically, the pressure may be checked to see if the periodic actuation maximum pressure is too low or too high. The artificial muscles may also be actuated/de-actuated according to the periodicity value that is updated in real-time, periodically, or remains static.

At block 1506, a determination may be made as to whether the amount of pressure applied by the child soothing device at maximum actuation during a periodic actuation differs from the received pressure value, which may be an updated periodic actuation pressure value. Continuing with this example, the user wants to maintain a consistent periodic actuation pressure applied by the child soothing device and thus waits as the pressure sensor compares the current periodic actuation pressure exerted by the child soothing device to obtain an updated pressure value.

If the periodic actuation pressure measured by the pressure sensor(s) differs from the received periodic actuation pressure value, then at block 1508 the actuation of the artificial muscles may be adjusted to, in turn, increase/decrease the periodic actuation pressure exerted by the child soothing device to then match the received pressure value. In some embodiments, there may be a threshold amount of difference to allow for small variations between the received periodic actuation pressure value and the measured periodic actuation pressure value.

Alternatively, if at block 1506 the periodic actuation pressure measured by the pressure sensor(s) matches the received periodic actuation pressure value, then at block 1510 the periodic actuation pressure amount is maintained to correspond to the received periodic actuation pressure value such that the baby experiences a consistent periodic heartbeat pressure. Updated pressure and/or periodicity values may be received at any time, which would correspond to restarting at block 1500 with the updated value(s).

It should now be understood that embodiments described herein are directed to child soothing devices that include one or more artificial muscles disposed under an outer layer of a soothing structure and communicatively coupled to a controller. Actuation of the one or more artificial muscles of the child soothing device applies a consistent periodic actuation pressure to simulate a heartbeat to a baby, as measured by a pressure sensor. The pressure sensor, communicatively coupled to the controller, outputs a current pressure value to the controller.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A child soothing device comprising:
    a controller;
    a soothing structure comprising an outer layer and an inner layer;
    one or more artificial muscles disposed between the inner layer and the outer layer of the soothing structure and communicatively coupled to the controller, wherein each of the one or more artificial muscles comprises:
        a housing comprising an electrode region and an expandable fluid region;
        a dielectric fluid housed within the housing; and
        an electrode pair positioned in the electrode region of the housing, the electrode pair comprising a first electrode and a second electrode, wherein the electrode pair is actuatable between a non-actuated state and an actuated state such that actuation from the non-actuated state to the actuated state directs the dielectric fluid into the expandable fluid region, expanding the expandable fluid region, thereby applying pressure to the inner layer of the soothing structure; and a pressure sensor affixed to the housing of the artificial muscle, the pressure sensor communicatively coupled to the controller and configured to output a pressure value to the controller, wherein the controller is configured to:
receive the pressure value output by the pressure sensor;
receive an updated pressure value at the artificial muscle to provide a periodic actuation pressure at the inner layer of the soothing structure based upon the pressure value; and
adjust the actuation of the artificial muscle to maintain the periodic actuation pressure at the inner layer of the soothing structure.

2. The child soothing device of claim 1, wherein the soothing structure comprises a wearable soothing structure.

3. The child soothing device of claim 2, wherein the wearable soothing structure is a swaddle comprising a central portion and a plurality of flaps, the central portion and the plurality of flaps each comprising a plurality of artificial muscles disposed therein.

4. The child soothing device of claim 1, wherein the soothing structure comprises a supportive soothing structure.

5. The child soothing device of claim 1, further comprising a warming element disposed under the outer layer of the soothing structure and communicatively coupled to the controller, wherein the controller is configured to output a warming value to the warming element.

6. The child soothing device of claim 1, wherein:
the first electrode and the second electrode each comprise two or more tab portions and two or more bridge portions;
each of the two or more bridge portions interconnects adjacent tab portions; and
at least one of the first electrode and the second electrode comprises a central opening positioned between the two or more tab portions and encircling the expandable fluid region.

7. The child soothing device of claim 6, wherein the two or more tab portions and the two or more bridge portions of the first electrode and the second electrode include two pairs of tab portions and two pairs of bridge portions, each bridge portion interconnecting a pair of adjacent tab portions, each tab portion diametrically opposing an opposite tab portion.

8. The child soothing device of claim 6, wherein:
when the electrode pair is in the non-actuated state, the first electrode and the second electrode are non-parallel to one another; and
when the electrode pair is in the actuated state, the first electrode and the second electrode are parallel to one another, such that the first electrode and the second electrode are configured to zipper toward one another and toward the central opening when actuated from the non-actuated state to the actuated state.

9. The child soothing device of claim 1, wherein the one or more artificial muscles disposed in the child soothing device comprise a plurality of artificial muscles arranged in a single layer.

10. The child soothing device of claim 1, wherein the one or more artificial muscles are configured to periodically actuate and de-actuate according to a periodicity parameter.

11. The child soothing device of claim 10, wherein the periodicity parameter determines a rate of actuation and de-actuation of the one or more artificial muscles.

12. A method for actuating a child soothing device, the method comprising:
providing a voltage using a power supply electrically coupled to an electrode pair of an artificial muscle, the artificial muscle disposed between an inner layer and an outer layer of a soothing structure of the child soothing device, wherein:
the artificial muscle comprises a housing having an electrode region and an expandable fluid region;
the electrode pair is positioned in the electrode region of the housing;
the electrode pair comprises a first electrode and a second electrode;
a dielectric fluid is housed within the housing; and
a pressure sensor is affixed to the housing and communicatively coupled to a controller;
applying the voltage to the electrode pair of the artificial muscle, thereby actuating the electrode pair such that the dielectric fluid is directed into the expandable fluid region of the housing and expands the expandable fluid region, thereby applying pressure to the inner layer of the soothing structure; and
receiving heartbeat data from a sensor device pertaining to a user wearing the sensor device, wherein the heartbeat data is used to reproduce a heartbeat of the user wearing the sensor device via actuation and de-actuation of the artificial muscle.

13. The method of claim 12 further comprising:
outputting, via the pressure sensor affixed to the housing of the artificial muscle and communicatively coupled to a controller, a pressure value to the controller;
receiving, from the controller, an updated pressure value at the artificial muscle to maintain a consistent amount of periodic actuation pressure at the inner layer of the child soothing device based upon the pressure value; and
adjusting the actuation of the artificial muscle to maintain the consistent amount of actuation pressure at the inner layer of the child soothing device.

14. The method of claim 13 further comprising:
receiving a current pressure value from the pressure sensor;
outputting the updated pressure value to the artificial muscle; and
modifying actuation of the artificial muscle based upon the updated pressure value to maintain the consistent amount of periodic actuation pressure at the inner layer of the child soothing device.

15. The method of claim 13, wherein the artificial muscle is one of a plurality of artificial muscles and the method further comprises adjusting the actuation of each of the plurality of muscles to maintain the consistent amount of periodic actuation pressure at the inner layer of the child soothing device.

16. A child soothing system comprising:
a child soothing device comprising:
a soothing structure comprising an outer layer and an inner layer;
network interface hardware communicatively coupled to a sensor device and configured to receive heartbeat data from the sensor device pertaining to a user wearing the sensor device;
one or more artificial muscles disposed between the inner layer and the outer layer of the soothing structure and communicatively coupled to a controller, wherein each of the one or more artificial muscles comprise:

a housing comprising an electrode region and an expandable fluid region;

a dielectric fluid housed within the housing; and an electrode pair positioned in the electrode region of the housing, the electrode pair comprising a first electrode and a second electrode, wherein the electrode pair is actuatable between a non-actuated state and an actuated state such that actuation from the non-actuated state to the actuated state directs the dielectric fluid into the expandable fluid region, expanding the expandable fluid region, thereby applying pressure to the inner layer of the soothing structure, and wherein the heartbeat data is configured to be utilized to reproduce a heartbeat of a user via actuation and de-actuation of the artificial muscle; and the sensor device, communicatively coupled to the child soothing device, the sensor device configured to:

detect the heartbeat of the user; and provide the heartbeat data corresponding to the user to the child soothing device.

17. The child soothing system of claim 16, wherein:

the first electrode and the second electrode each comprise two or more tab portions and two or more bridge portions;

each of the two or more bridge portions interconnects adjacent tab portions; and at least one of the first electrode and the second electrode comprises a central opening positioned between the two or more tab portions and encircling the expandable fluid region.

* * * * *

UNITED STATES PATENT AND TRADEMARK OFFICE
CERTIFICATE OF CORRECTION

| | | |
|---|---|---|
| PATENT NO. | : 12,150,493 B2 | Page 1 of 1 |
| APPLICATION NO. | : 17/160548 | |
| DATED | : November 26, 2024 | |
| INVENTOR(S) | : Erin J. Rutledge and Michael P. Rowe | |

It is certified that error appears in the above-identified patent and that said Letters Patent is hereby corrected as shown below:

On the Title Page

Column 2, item (57), abstract, Line(s) 1, after "structure", insert --that--.

In the Specification

In Column 7, Line(s) 59, delete "stoke" and insert --stroke--, therefor.

In Column 8, Line(s) 43, delete "so" and insert --as--, therefor.

In Column 17, Line(s) 52, delete "exert" and insert --and exerted--, therefor.

In the Claims

In Column 20, Line(s) 31, Claim 13, after "claim 12", insert --,--.

In Column 20, Line(s) 43, Claim 14, after "claim 13", insert --,--.

Signed and Sealed this
Eleventh Day of February, 2025

Coke Morgan Stewart
*Acting Director of the United States Patent and Trademark Office*